United States Patent [19]

Takeo et al.

[11] 4,447,601

[45] May 8, 1984

[54] PROCESSED STARCH, PROCESS FOR PREPARING SAME AND USE OF SAME IN MEDICINES

[75] Inventors: Kimihiko Takeo; Tooichiro Hirano; Fumihiko Sato, all of Nobeoka, Japan

[73] Assignee: Asahi Kasei Kogyo Kabushiki Kaisha, Osaka, Japan

[21] Appl. No.: 424,184

[22] Filed: Sep. 27, 1982

Related U.S. Application Data

[62] Division of Ser. No. 272,253, Jun. 10, 1981, Pat. No. 4,383,111.

[30] Foreign Application Priority Data

Jun. 12, 1980 [JP] Japan .................................. 55-79266

[51] Int. Cl.$^3$ .......................... C08L 3/02; C08B 31/00
[52] U.S. Cl. .................................... 536/102; 106/210; 106/213
[58] Field of Search ................. 536/102; 106/210, 213

[56] References Cited

U.S. PATENT DOCUMENTS

| | | | |
|---|---|---|---|
| 2,614,945 | 10/1952 | Krisan | 106/210 |
| 3,071,492 | 1/1963 | Satterly | 536/102 |
| 3,622,677 | 11/1971 | Short et al. | 106/210 |
| 4,072,535 | 2/1978 | Short et al. | 106/210 |
| 4,104,212 | 8/1978 | Bruner | 536/102 |
| 4,104,213 | 8/1978 | Chiang et al. | 536/102 |

*Primary Examiner*—Ronald W. Griffin
*Attorney, Agent, or Firm*—Armstrong, Nikaido, Marmelstein & Kubovcik

[57] ABSTRACT

A processed starch useful as a disintegrant to be incorporated into medicines is provided. The processed starch consists essentially of substantially non-birefringent starch powder which substantially retains the shell film structure of green starch granules. The starch powder has a particle size distribution substantially free of a fraction having a size of 48 Tyler standard sieve mesh or having a larger size, and has a bulk density of at least about 0.25 g/cc, a cold water-soluble component content of less than 10% by weight, a swelling volume of about 3 to about 15 ml/g and a water retention of at least about 2. The processed starch is prepared by a process wherein water and, if necessary, an organic solvent is added to green starch to form a dispersion having a solid a component concentration of not more than 60%; the dispersion is heated to render the green starch granule non-birefringent by swelling the green starch granule without destruction of the shell film structure thereof; and then, the dispersion is dried without destruction of the shell film structure.

10 Claims, No Drawings

PROCESSED STARCH, PROCESS FOR PREPARING SAME AND USE OF SAME IN MEDICINES

This is a division, of application Ser. No. 272,253, filed June 10, 1981, now U.S. Pat. No. 4,383,111, issued May 10, 1983.

BACKGROUND OF THE INVENTION

1. Field of the Invention

This invention relates to a novel processed starch useful as a disintegrant to be incorporated in medicines, and also to a process for preparing such processed starch. It relates to the application of the processed starch as a disintegrant in medicines.

The processed starch according to the present invention is characterized as exhibiting appropriate water-absorbing and swelling properties, which are imparted thereto by physical treatments alone without any chemical modification. When the processed starch of the present invention is applied to the manufacture of solid pharmaceutical preparations such as tablets, granules, fine granules, pills and capsules, irrespectively of whether a dry method, a wet method or a semi-dry method is adopted, a rapid disintegrating property is given to these pharmaceutical preparations and a substantial bulking effect can be obtained. The processed starch of the present invention is further characterized in that when it is used for the manufacture of tablets, not only an effect of shortening the disintegration time of the tablets but also an effect of improving the disintegration pattern of the tablets to produce a good dissolution state of the active ingredient is also obtained.

2. Description of the Prior Art

As typical instances of disintegrants conventionally used for pharmaceutical preparations, there can be mentioned cellulose derivatives such as calcium carboxymethyl cellulose, low-viscosity sodium carboxymethyl cellulose, hydroxypropyl cellulose having a low degree of substitution and crosslinked sodium carboxymethyl cellulose; vegetable gums such as guar gum and sodium alginate; crosslinked polyvinyl pyrrolidone; cation exchange resins, and starch derivatives such as hydroxypropyl starch and carboxymethyl starch. Most of these disintegrants are chemical products, and even disintegrants derived from natural products such as cellulose and starch are obtained through chemical modification. Starch and cellulose which have not been subjected to a modification treatment with a chemical but show a good disintegrating activity have heretofore not been found. For example, cellulose per se has a moldability and is used as a binder in the field of medicines, but it is poor in its disintegrating activity.

As a cheap disintegrant which has not undergone chemical modification, there can be mentioned green starch, but since green starch is poor in the swelling property, in order to impart a rapid disintegrating property to a molded product, it is necessary to use green starch in large quantities, with the result that as is well-known, such defects as occurrence of the capping phenomenon and softening of the molded product with the lapse of time arise.

$\alpha$-starch which is rendered completely soluble in cold water by a heat treatment or acid treatment of green starch is sometimes used as a disintegrant. However, when $\alpha$-starch is used as a disintegrant, while an aqueous disintegrating medium such as water penetrates into fine pores of the molded product, $\alpha$-starch is dissolved in the disintegrating liquid to drastically increase the viscosity of the disintegrating medium, with the result that smooth penetration of the disintegrating liquid is inhibited and a rapid disintegrating property can hardly be imparted to the molded product.

Another starch selected from natural starches which are abundant resources is used as a disintegrating agent. For example, U.S. Pat. No. 3,622,677 proposes a starch valuable as a binder-disintegrant, which consists of a mixture of birefringent granules and non-birefringent fragments, in which some aggregates of granules and fragments are present, the cold water solubility is about 4 to about 40% by weight, the swelling power of the dry product is about 2.5 to about 12, the bulk density is about 0.5 to about 0.7 g/ml, the moisture content is about 9 to about 16% based on the total weight, and the particle size may be substantially larger than 40 mesh but the particle size distribution is such that at least 90%, based on the total weight, of the powder has a size of more than 80 mesh, about 10 to about 70% of the powder has a particle size of more than 270 mesh and about 30 to about 90% of the powder has a particle size of less than 270 mesh. This starch is obtained by making compact a starting starch having a water content of about 20 to about 50% by weight at a temperature of 20° to 50° C. by a differential roll mill or parallel roll mill, and then drying and pulverizing the so treated starch. The starch obtained according to this method, however, is defective in that when a molded product is prepared according to the so-called wet granulation method where granulation is carried out after addition of water and the granulation product is compressed, no substantial disintegrating activity is attained. Furthermore, as disclosed in the above U.S. Patent, in order for the starch to exert a sufficient activity as a binder when it is incorporated into a tablet as a pharmaceutical molded product, various requirements should be satisfied. For example, the starch should be present in an amount of at least 50% based on the total weight of the tablet, and this starch should preferably be a sole binder to be added to the pharmaceutical composition. If these requirements are not satisfied, no satisfactory binding and disintegrating actions can be attained, and the freedom of selection of the recipe for a molded product is considerably restricted.

Furthermore, Japanese patent publication No. 5725/78 proposes a process for preparing granules and tablets by using $\alpha$-starch having an $\alpha$-type surface as a binder and a disintegrant. The starch described in this Japanese Patent Publication is a starch which has a surface modified to the $\alpha$-type but retains the $\beta$-type structure in the interior, which is prepared by a method comprising coating the surface of $\beta$-starch, that is, green starch, with $\alpha$-starch, a method comprising jetting high pressure steam to green starch fluidized in a fluidized layer or a method comprising suspending green starch in water and spraying the suspension in an air atmosphere having a temperature of 200° to 400° C. Since the surface of the obtained starch has a $\alpha$-type structure, the starch has a good binding property, but a long time is required for an disintegrating medium to pass through the $\alpha$-type portion and arrive at the $\beta$-type portion, or while the disintegrating liquid penetrates into fine pores of the molded product, the $\alpha$-type portion is dissolved in the disintegrating medium to increase the viscosity thereof. Accordingly, since penetration of the disintegrating medium is thus blocked and the disintegrating action is not satisfactory. As taught in "Handbook of Starch Chemistry," page 35, compiled by Jiro Nikuni and published by Asakura Shoten in 1977, α-starch has ordinarily high reactivity with enzymes and chemicals. Accordingly, if starch having a surface modified to the α-type is incorporated into medicines, the application is restricted because of such high reactivity.

It is known that a starch is heat-treated and the heat-treated starch is used as a food additive. For example, Japanese Laid-Open Patent Application No. 28691/80 (claiming the Convention priority based on British Patent Application No. 31695/78) discloses a technique of heating a root starch or tuber starch such as potato starch, tapioca starch or aloe root in the presence of 18 to 25% of water at a temperature of about 90° to about 120° C. to form a retarding type thickener and utilizing the thickener for preparation of sauces, gravy sauces or white sauces. As disclosed in this Japanese Laid-Open Patent Application, a most practical and industrial process for the preparation of starch having a retarding thickening function is one in which starch is merely heated in a closed heating apparatus at an ordinary water content (not in the state of an aqueous slurry) and a hydrothermal treatment is advanced to a desirable degree.

As shown in Comparative Examples given hereinafter, the so-obtained thickener has a small expanded volume but a high content of a cold water-soluble component, and it has the same defects as described above with respect to the product disclosed in Japanese Patent Publication No. 21471/79, which is the equivalent of U.S. Pat. No. 3,622,677. Thus, the thickener cannot be a disintegrant as intended in the present invention.

SUMMARY OF THE INVENTION

It is therefore a primary object of the present invention to provide a novel processed starch which provides a prompt disintegrating action when it is used for a medicine in the form of a tablet, granule, fine granule or capsule, which gives a preferred disintegration pattern to improve the dissolution rate of an active ingredient particularly when it is used for a tablet and which can also be used as an excipient and can exert a substantial bulking effect.

In accordance with the present invention, there is provided a processed starch consisting essentially of substantially non-birefringent starch powder which substantially retains a shell film structure of green starch granule, said starch powder having a particle size distribution substantially free of a fraction having a size of 48 Tyler standard sieve mesh or having a larger size, preferably free of a fraction having a size of 60 Tyler standard sieve mesh or having a large size, and said starch powder having a bulk density of at least about 0.25 g/cc, preferably at least about 0.3 g/cc, a cold water-soluble component content of less than 10% by weight, preferably less than 5% by weight, a swelling volume of about 3 to about 15 ml/g, preferably about 7 to about 15 ml/g, and a water retention of at least about 2, preferably at least about 3.

DESCRIPTION OF THE PREFERRED EMBODIMENTS

The starch of the present invention consists essentially of substantially non-birefringent starch powder. All the green starches present in vegetable cells have a granular structure, and such green starch is called "starch granule." When this green starch granule is poured into water and observed by a polarizing microscope, it shows a birefringent characteristic inherent of a crystalline substance. But, the starch powder of the present invention is substantially non-birefringent, and therefore, the crystallinity is lost and the starch is amorphous.

The above-mentioned green starch granule has a film shell. The starch powder of the present invention also retains this film shell structure. Rupture of the film is not caused but the form of the starch granule is maintained. Accordingly, respective particles of the starch powder can be discriminated.

Non-birefringent starch in which the shell film structure is broken is irreversibly swollen (dissolved) in water, with the result that the viscosity of the liquid is increased and the reactivity of the starch with an enzyme or a chemical is enhanced. In contrast, in the starch powder of the present invention, since the shell film structure is not broken but retained, elution of amylose as the water-soluble component is controlled and thus the content of the cold water-soluble components is low. When this starch powder is poured into water again, it absorbs water rapidly to swell again because it is amorphous. Moreover, since this starch powder does not become viscous paste even when it absorbs water, it can act as an excellent disintegrant.

The processed starch powder of the present invention has a cold water-soluble component content (the measurement method will be described hereinafter) of less than 10% by weight, preferably less than 5% by weight, especially preferably less than 4% by weight. If the cold water-soluble component content is higher than 10% by weight, the stickiness is increased when the starch absorbes moisture, and the disintegrating effect is reduced. When the cold water-soluble component content is lower than 4% by weight, an especially good disintegrating activity is obtained. The cold water-soluble component content of green starch granule is about 0.2 to about 0.4% by weight. Accordingly, in the starch of the present invention, the cold water-soluble component content cannot be lower than this level.

The processed starch powder of the present invention has an swelling volume (the definition and measurement method will be described hereinafter) of about 3 to about 15 ml/g, preferably about 7 to about 15 ml/g, especially preferably about 8 to about 11 ml/g. The swelling volume of green starch granule is about 1 to about 2 ml/g. When a starch having an swelling volume smaller than about 3 ml/g, is used, no prompt disintegrating property can be given to the resulting molded product. Since the processed starch powder of the present invention is neither chemically modified nor gelatinized, the upper limit of the swelling volume is about 15 ml/g.

The processed starch powder of the present invention has a water retention (the definition and measurement method will be described hereinafter) of at least about 2, preferably at least about 3, and the water retention of the processed starch powder of the present invention is ordinarily in the range of from 4 to 7. A green starch granule exhibits a water retention of below 2. By virtue of this characteristic, the processed starch powder of the present invention can impart not only a good disintegrating property but also a good water-retaining property to the resulting molded product.

The processed starch powder of the present invention should not contain coarse particles having a size exceeding 48 Tyler standard mesh (hereinafter referred to as "mesh" for brevity), and preferably, at least 95% by weight, especially 100% by weight, of the processed starch powder should pass a 60-mesh sieve. If the granule size is too large, the deviation of the disintegration time among particles in the resulting molded product is undesirably increased.

The processed starch powder of the present invention should have a bulk density of at least about 0.25 g/cc, preferably at least 0.3 g/cc. The true density of green starch granule is about 1.6 g/cc, and the bulk density of the processed starch powder of the present invention does not exceed this value. If the bulk density is lower than about 0.25 g/cc, the moldability of the processed starch at the compression of the dry molding method is not good and the flowability of the processed starch as powder is reduced.

The process for the preparation of processed starch powder for use in manufacture of pharmaceutical preparations according to the present invention will now be described.

The process for the preparation of processed starch powder according to the present invention is characterized in that green starch granule is heated in the presence of water and, if necessary, an organic solvent to swell the green starch granule without destruction of the abovementioned shell film structure and the heated starch granule is then dried without destruction of the shell film structure.

Any of the terrestrial starches, namely grain starches, such as corn starch, wheat starch and rice starch, can be used as the starting material in the present invention. From the viewpoint of easy availability and good adaptability to the process of the present invention, corn starch is especially preferred. A root starch or tuber starch such as potato starch or tapioca starch has a large swelling property, but use of such starch is not preferred because preparation conditions are restricted within very narrow ranges and properties and effects or such starch are degraded with the lapse of time, especially when it absorbs moisture. A mixture of two or more starches can optionally be used in the present invention, but difficulties are encountered because the swelling rate in water differs among the starches used. However, a mixture of two or more of the processed starch products obtained according to the present invention can advantageously be used for the molding operation.

The particle size of the starting starch granule is preferably determined according to the intended particle size of the processed starch product. Of course, the obtained processed starch may be classified by sieving or the like.

At the step of heating in water and the drying step in the process of the present invention, it is necessary to avoid destruction of the shell film structure of the starting starch granule, which results in irreversible swelling or dissolution and conversion of the aqueous solution to a paste. In short, gelatinization of starch granules should be avoided. It is admitted that the gelatinization temperature of starch granules varies to some extent according to the measurement method, the kind of starch, the particle size, the place of production and the climate conditions at its harvesting time. Values of gelatinization-starting temperatures of starches determined by tracing the light transmittances of suspensions by a photopasteographical apparatus (supplied by Hirama Rika Kenkyusho K.K.) are shown in Table 1 (cited from page 36 of handbook of Starch Chemistry).

TABLE 1

| Gelatinization-starting Temperature of Various Starches | |
|---|---|
| Kind of Starch | Gelatinization-starting Temperature (°C.) |
| Potato starch | 61.0 |
| Tapioca starch | 65.4 |
| Sweetpotato starch | 65.8 |
| Corn starch | 66.8 |
| Wheat starch | 58.0 |

For example, if it is intended to swell starch without destruction of the shell film structure by heating the starch in the presence of an excessive amount of water, as in the case of a slurry having a water content of at least 70%, preferably at least 80%, the heating temperature should not be elevated to a level higher by at least 10° C. than the gelatinization temperature shown in Table 1. Furthermore, if a green starch-water mixture having a relatively low water content, for example, about 30 to about 70%, is heated, it is possible to perform heating at a temperature approximating to the boiling point of water, that is, about 80° to about 140° C., but in this case, uniform heating is so difficult that the product tends to contain the birefringent granules with the non-birefringent ones. Accordingly, if uniform heating is desired, it is preferred that heating be carried out at a relatively low temperature in the presence of water in such an excessive amount as will provide at least a pasty or slurry flowable mixture. It is natural that the intended effects of the present invention cannot be attained only by dipping starch in water, and heating should be carried out at a temperature of at least 50° C., preferably approximately at the gelatinization-starting temperature. The heating time is not particularly critical in the present invention. If it is intended to perform heating at a certain temperature, the heating time may freely be selected from a broad range of from a short time of 1 to 2 minutes to a long time of several hours. Of course, a longer heating time may be adopted. From the viewpoint of the energy efficiency, a shorter heating time is preferred. However, for example, when the processed starch powder obtained by performing heating for a short time and then drying heated starch is observed by a microscope, on rare occasions, the presence of indefinite birefringent granules in very small proportions is detected. More specifically, less than about 10 birefringent granules appear per 100 of heat-treated granules. It is considered that the appearance of such birefringent granules is due to the fact that green starch granules have a broad particle size distribution. However, the birefringent characteristic of such granules is more ambiguous or weaker than the clear birefringent characteristic of green starch granules, and therefore, these granules can be clearly distinguished. Even the starch powder containing ambiguous birefringent granules in very small proportions should be considered to be included in the scope of the present invention. Of course, it is preferred that the ratio of granules in such transition state be as low as possible.

In the present invention, the heating method is not particularly critical, and also the amount of water to be made present is optional. For example, water contents may vary within a broad range of from a level providing a very dilute slurry to a level providing a slightly wet starch-water mixture, for example, about 30% by weight. However, it is ordinarily preferred that the water content in the starch-water mixture is at least about 40% by weight, especially at least about 70% by weight, more preferably at least about 80% by weight. In order to ensure uniform heating at the heating step, stirring, shaking or mixing may freely be conducted. However, in the present invention, since it is important that starch should be heated and then dried without destruction of the majority of granules, it is best not to mix or knead using an apparatus exerting a strong shearing force, such as a differential roll mill or a parallel roll mill.

In order to facilitate the drying operation at the subsequent drying step described hereinafter, an organic solvent may be used in combination with water at the heating step. In this case, a single organic solvent or a mixture of two or more of organic solvents may be used, and either an organic solvent compatible with water or an organic solvent incompatible with water may be used. When an organic solvent compatible with water is used in combination with water, it sometimes happens that the gelatinization-starting temperature of starch granules becomes higher than the gelatinization-starting temperature observed when water alone is used. Also in this case, heating is carried out so that the starch particles are rendered amorphous, while confirming retention of the shell film structure in the starch particles by the polarizing cross measurement described hereinafter.

Specific embodiments of the process of the present invention will be described in Examples given hereinafter. Hereupon, however, one embodiment is described. Ethanol is mixed with water, and corn starch is heated by using an aqueous solution of ethanol at a concentration of about 50 to about 80% by weight. If heating is carried out at about 90 to about 150° C., the heating time is ordinarily several minutes to scores of minutes. When the so-heated starch is dried, intended processed starch of the present invention can be obtained. Of course, the scope of the present invention is by no means limited by this embodiment.

Any organic solvents having a boiling point lower than that of water may be used in combination with water, but needless to say, an organic solvent which is low in oral toxicity is preferred.

Factors that should be taken into account at the drying step are the drying temperature and the drying speed. For example, if starch suspended in a slurry state is dried at an extremely high temperature exceeding the gelatinization-starting temperature at a low drying speed, the intended effects of the present invention cannot be obtained. When a starch-water mixture having an excessive water content, for example, a dilute slurry, is heated, an apparatus capable of instantaneously producing the falling rate drying state, such as a flash dryer or spray dryer, should be used. Of course, there may be adopted a method in which drying is performed at a low speed at a temperature lower than the gelatinization-starting temperature or other known methods such as the reduced pressure drying method, the vacuum drying method, the vacuum freeze-drying method and the organic solvent substitution drying method.

The starch powder of the present invention should satisfy the requirement that when the starch is examined by a microscope according to the method described hereinafter, the majority of granules thereof are not destroyed. Damage to the starch granules occurs when green starch granules are damaged or when the temperature adopted for the step of heating in the presence of water or the subsequent drying step is too high. Granules damaged by too high a temperature at the heating step cannot be restored at the subsequent drying step. Accordingly, when the obtained starch powder is examined according to the method described hereinafter, the degree of damage caused to particles at the drying step can be known.

Methods for application of the processed starch of the present invention will now be described.

The processed starch of the present invention satisfying the above-mentioned requirements has a good swelling property and can be used at a disintegrant for molded products in various fields. The processed starch of the present invention can be applied particularly effectively to molded products such as tablets, granules and fine granules of medicines, which are administered to human bodies and are required to disintegrate promptly in body fluids such as gastric juice and enteric juice. When the processed starch of the present invention is added to a medicine to impart a disintegrating property thereto, this object can be attained by incorporating the processed starch in an amount of about 1 to about 10% by weight, preferably 3 to 10% by weight, based on the total weight of the medicine. Since the processed starch of the present invention has no medicinal effect, it is permissible to incorporate the processed starch in an amount larger than 10% by weight. In this case, the processed starch can also act as a bulking agent.

The processed starch of the present invention is different from untreated corn starch or the like, in that even if the processed starch is incorporated into tablets in a large amount, neither capping nor lamination is caused at all. Accordingly, in order to obtain a bulking effect, the processed starch of the present invention may be added in an amount exceeding 10% by weight together with other pharmaceutical additives, such as lactose, calcium secondary phosphate and glucose. In this case, of course, an improved disintegrating effect can be attained.

In the case where the processed starch of the present invention is used for tablets, especially good results are obtained if it is used in combination with microcrystalline cellulose. Namely, by virtue of the excellent water-absorbing and swelling properties of the processed starch of the present invention and excellent moldability and water-inducing property of microcrystalline cellulose, it becomes possible to manufacture very hard tablets having a much reduced tendency to be powdered and also having a very short disintegration time. In this case, both the processed starch of the present invention and microcrystalline cellulose may be added in the powdery state independently to a pharmaceutical preparation, or they may be added in the form of a composite product obtained by suspending or dispersing the processed starch of the present invention and microcrystalline cellulose in an aqueous medium with stirring to form a homogeneous suspension or dispersion and drying the suspension or dispersion by an appropriate drying method, for example, spray drying, organic solvent substitution drying, vacuum freeze-drying or hot air drying.

A pharmaceutical composition in which the processed starch powder of the present invention has thus been incorporated is granulated or molded according to customary procedures, and fine granules, granules, tablets or pills can be obtained. These molded products may be film coated, sugar-coated or wax-coated.

When a pharmaceutical molded product obtained by using the processed starch of the present invention is placed in a disintegrating liquid, it disintegrates as if it dissolves from the surface thereof. In short, this molded product shows a so-called "dissolution type disintegration pattern," and the dissolution efficiency of the pharmaceutically active ingredient is very high. This dissolution type disintegration pattern is not obtained when conventional green starch or α-starch is incorporated into a pharmaceutical preparation. In short, this system merely shows a block type disintegration pattern. That is, the dissolution rate of the pharmaceutically active ingredient is often reduced when conventional green starch or α-starch is used. Development of a disintegrant capable of imparting a dissolution type disintegration pattern to molded products has been desired in the pharmaceutical industry. The present invention can fully meet this desire.

In the processed starch of the present invention, the outer shell film structure is retained, and even if it comes in contact with water, elution of amylose is controlled to a low level. Accordingly, even if the processed starch of the present invention is incorporated in a pharmaceutical preparation, the stability is much higher than the stability observed when α-starch is used.

The definitions of the special terms used in the present invention and the measurement methods will now be described.

Cold Water-Soluble Component Content 3 g (absolutely dry base) of a sample is precisely weighed, and 297 ml of pure water maintained at 25° C. is added thereto and the mixture is subjected to high-speed stirring at 1500 rpm for 2 minutes. The obtained suspension is divided into 6 equal parts. Each sample suspension is transferred to a round-bottom centrifugal separation tube and is subjected to centrifugal separation at 2000 rpm for 15 minutes. 30 ml of the supernatant is collected and transferred to a wide-mouthed weighing bottle, and the supernatant is dried and evaporated on a steam bath. Then, the bottle is dried at 110° C. until the weight of the bottle becomes constant. The weight of the dry substance on the bottle is multiplied by 1000, and the product is divided by the original weight of the starting dry sample. The obtained value is the cold water-soluble component content of the starch powder. A mean value (n=3 to 6) is calculated and this mean value is adopted.

Swelling Volume 5 g of a sample is charged in a 100-ml of capacity graduated measuring cylinder equipped with a common plug, and about 80 ml of deionized water maintained at 25° C. is added. The mixture is shaken to remove bubbles, and deionized water is further added so that the total amount is 100 ml. The cylinder is plugged and allowed to stand still for 24 hours. The volume of the sample swollen by absorption of water is read. The read value is divided by 5, and the quotient is adopted as the swelling volume of the sample.

Water Retention

An aqueous dispersion is prepared in the same manner as described above with respect to the measurement of the swelling volume, and the aqueous dispersion is transferred to a centrifugal sedimentation tube and subjected to centrifugal separation at 4500 rpm for 30 minutes. The supernatant is removed, and the weight (W, g) of the wet sediment is measured. Then, the sediment is completely dried and the weight (Wo, g) is measured. The water retention is calculated according to the following formula:

Water retention = $W/W_o$

Observation of State of Destruction (Damage) of Granules

The state of destruction of starch granules is observed according to the procedure described on page 289 of "Handbook of Starch Chemistry." That is, 0.5 g of a sample is charged in a centrifugal sedimentation tube having a capacity of 10 ml, and about 2 ml of an 1% aqueous solution of Safranine 0 (supplied by Tokyo Kasei Kogyo K.K.) is added. The mixture is sufficiently stirred by a glass rod and is then allowed to stand still for 15 minutes to effect dyeing. Then, distilled water is added to the mixture and centrifugal separation is repeated 3 to 5 times to wash away the excessive dye. The so-washed sample is transferred onto a slide glass and an 1% aqueous solution of Nippon Sky Blue (supplied by Yamato Kakosho K.K.) is added and mixed sufficiently with the sample. Then, a cover glass is placed and the sample is observed by a microscope.

The color index numbers of Safranine 0 and Nippon Sky Blue are 50240 and 24400, respectively.

The processed starch powder of the present invention does not show a pink dyeing color as shown by green starch or a deep blue dyeing color as shown by completely gelatinized starch, but it shows a reddish violet-to-bluish violet dyeing color. Of course, the processed starch powder does not show a two-phase dyeing state as shown by β-starch having an α-type surface, in which the α-type portion shows a blue color and the β-type portion shows a pink color. Furthermore, the processed starch powder of the present invention does not show a mixed dyeing state as shown by starch comprising birefringent granules and non-birefringent granules, in which some portions show a pink color, other portions show a blue color and still other portions show both colors. Namely, in the processed starch of the present invention, respective granules show a uniform reddish violet-to-bluish violet color from the outer layer to the interior, and in respective granules, the outer shell is left in the form of a film, though it is elongated to some extent. Accordingly, it is confirmed that the structure of the processed starch of the present invention is apparently different from the structure of gelatinized slurry starch.

When starches other than the preferred starch of the present invention, for example, β-starch having an α-type surface or starch comprising birefringent granules and non-birefringent granules, are dyed and observed by a microscope in the above-mentioned manner, at the step of washing away the excessive dye after dyeing with Safranine 0, the water-soluble α-portion is damaged or exposed amylose is washed away by water, with the result that the number or ratio of granules dyed in a deep blue color is reduced and it sometimes happens that only granules dyed in a pink color are predominantly observed. Accordingly, this should be taken into account when the microscopic observation is carried out in the above-mentioned manner.

Furthermore, the color of the dyed sample is slightly changed according to the light source used for the microscopic observation, and also this fact should be taken into account. It is preferred that natural light should be used at the light source as much as possible.

The present invention will now be described in detail with reference to the following Examples that by no means limit the scope of the present invention.

EXAMPLE 1

Pharmacopoeial corn starch was dispersed in water at a solid concentration of 5, 10 or 15% by weight. Each resulting slurry was heated at 65° C. for 20 minutes. Then, each slurry was sprayed at a speed of 5 l/hr in an atmosphere having an inlet temperature of about 180° C. and an outlet temperature of about 90° C. by using a bench-scale spray dryer having a two-fluid nozzle. The physical properties of the so-obtained samples A-1, A-2 and A-3 are shown in Table 2, below.

EXAMPLE 2

Pharmacopoeial corn starch was dispersed in water at a solid concentration of 30% by weight and the dispersion was heated at 67° C. for 30 minutes. The heated dispersion was transferred onto a tray and dried in a hot air dryer maintained at 40° C. until the water content was reduced to about 4% by weight. Then, the dried product was passed through a hammer mill twice. The sample obtained after one passage through the hammer mill was designated as sample B-1, and the sample collected after passing the dried product through the hammer mill twice was designated as sample B-2. The physical properties of these samples are shown in Table 2, below.

EXAMPLE 3

Pharmacopoeial corn starch was dispersed in water at a solid concentration of 30% by weight and the dispersion was heated at 67° C. for about 30 minutes. The heated suspension was placed into methyl alcohol in a volume about 3 times the volume of the dispersion. The mixture was filtered and placed into an excessive amount of methyl alcohol to effect substitution dehydration. Then, the dehydrated product was filtered and air-dried, and coarse granules were removed by using a 60-mesh sieve to obtain a sample C. The physical properties of this sample are shown in Table 2, below.

COMPARATIVE EXAMPLE 1

Pharmacopoeial corn starch was dispersed in water at a solid concentration of 10% by weight and heated at 76° C. for 60 minutes with violent stirring. The dispersion was placed in water in an amount equal to the amount of the dispersion, and the mixture was cooled and filtered, and the recovered residue was freeze-dried. The obtained dried product was pulverized by a hammer mill to obtain a sample D.

EXAMPLE 4

Pharmacopoeial corn starch was mixed with water to adjust the water content to 40% by weight (solid concentration of 60% by weight). The mixture was heated at 110° C. for 30 minutes in a closed vessel, subjected to substitution dehydration with ethanol and dried in a hot air dryer maintained at 60° C. until the water content was reduced to about 4%. The dried product was passed through a speed mill (supplied by Fuji Powder K.K.) and coarse particles were removed by using a 60-mesh shieve to collect a sample E. The physical properties of this sample are shown in Table 2, below.

Comparative Example 2

Water was added to pharmacopoeial corn starch so that the water content was 24 to 25%. The mixture was extruded through a pellet mill (supplied by Fuji Powder K.K.) and then dried so that the water content was reduced to about 7%. The dried product was pulverized by a hammer mill and the powdery product passing through a 100-mesh sieve was collected. The powdery product was mixed with water in a ribbon blender to adjust the water content to 12% and obtain a compacted starch powder (sample F) (see EXAMPLE 1 of U.S. Pat. No. 3,622,677. The physical properties of the sample are shown in Table 2, below.

Comparative Example 3

Pharmacopoeial corn starch was treated and granulated by using a corn starch liquid as a binder in a fluidized layer granulator (Model Uni-grat supplied by Ohkawara Seisakusho K.K.) according to customary procedures to obtain a powdery β-type starch having an α-type surface (sample G). The ratio of the sprayed α-starch was about 14%. The physical properties of this sample are shown in Table 2.

COMPARATIVE EXAMPLE 4

An aqueous slurry containing 3% by weight of pharmacopoeial corn starch was heated at 95° C. to effect complete gelatinization, and the resulting slurry was spray-dried according to the same method as described in Example 1. Coarse granules were removed by using a 60-mesh sieve and a sample H was recovered. The physical properties of the sample are shown in Table 2, below.

TABLE 2

| | | | Physical Properties of Various Samples | | | | |
|---|---|---|---|---|---|---|---|
| Sample | Content (%) of Residue on 60-Mesh Sieve | Bulk Density (Loose) (g/cc) | Cold Water-Soluble Component Content (%) | Swelling Volume (ml/g) | Birefringent Characteristic | Destruction of Granules | Water Retention |
| Examples of Present Invention | | | | | | | |
| A-1 | 0 | 0.36 | 0.8 | About 8.8 | No Substantial polarizing cross hairs | Violet color | About 4.9 |
| A-2 | 0.1 | 0.50 | 0.9 | About 8.9 | No substantial polarizing cross hairs | Violet color | About 5.7 |
| A-3 | 0.3 | 0.55 | 1.0 | About 9.2 | No substantial polarizing cross hairs | Violet color | About 6.1 |
| B-1 | 7.4 | 0.67 | 1.2 | About 7.8 | No substantial polarizing cross hairs | Bluish violet color | About 5.3 |
| B-2 | 2.3 | 0.66 | 1.2 | About 8.3 | No substatial | Bluish | About 5.3 |

TABLE 2-continued

| | | | Physical Properties of Various Samples | | | | |
|---|---|---|---|---|---|---|---|
| Sample | Content (%) of Residue on 60-Mesh Sieve | Bulk Density (Loose) (g/cc) | Cold Water- Soluble Component Content (%) | Swelling Volume (ml/g) | Birefringent Characteristic | Destruction of Granules | Water Retention |
| C | 0 | 0.30 | 1.1 | About 9.5 | polarizing cross hairs No substantial polarizing cross hairs | violet color Violet color | About 5.9 |
| E | 0 | 0.42 | 4.3 | About 7.0 | 10% particles showing polarizing cross hairs | Reddish violet color with slight damage | About 3.8 |
| Comparative Examples | | | | | | | |
| D | 0.1 | 0.37 | 15.3 | About 16 | No substantial polarizing cross hairs | Deep blue color with slight damage | About 3.8 |
| F | 0.3 | 0.56 | 9.6 | About 7.2 | 40–50% of particles showing polarizing cross hairs | Co-presence of blue and pink colors | About 4.4 |
| G | 2.1 | 0.47 | 2.5 | About 3.8 | Most particles showing polarizing cross hairs | Co-presence of blue and pink colors and two colors-mixed portion | About 2.3 |
| H | 0 | 0.55 | 32.0 | About 16 | No polarizing cross hairs | Deep blue color | About 3.4 |
| CS* | 0 | 0.45 | 0.3 | Less than 2 | All granules showing polarizining cross hairs | Clear pink color | About 1.6 |

Note
*CS stands for unprocessed green starch (CS given hereinafter has the same meaning)

EXAMPLE 5

To 950 parts of a composition comprising 200 parts of pharmacopoeial phenacetin powder, 400 parts of pharmacopoeial microcrystalline cellulose, 345 parts of pharmacopoeial crystalline lactose and 5 parts of pharmacopoeial magnesium stearate were added 50 parts of each of the samples shown in Table 2, and they were blended according to customary procedures. The mixture was directly tableted by using a rotary tableting machine, Model RT-S22 (supplied by Kikusui Seisakusho K.K.; punch diameter of 8 mm, 12R), so that a mean value of the tablet weight, as calculated from the weights of twenty tablets, was 250±10 mg. The properties of the obtained tablets were evaluated according to methods described below. The obtained results are shown in Tables 3 and 4, below.

Deviation of Weights of Tablets:
Twenty tablets were precisely weighed and the coefficient of variance (n=20) was determined.

Hardness:
Twenty tablets were subjected to the destruction test by using a Kiya type hardness tester (unit: Kg), and the average value was calculated.

Disintegration Time:
The disintegration time was determined according to the method described in the 9th edition of the Japanese Pharmacopoeia by using bare tablets. Incidentally, the test was carried out in the state where the disc was taken out. The average value was calculated (n=6).

Disintegration Pattern:
The disintegration pattern was observed according to the following two methods.

(1) Stationary method:
A disintegrating liquid was charged in a Petri dish and one tablet was sunk in the liquid at the center of the dish. The tablet was allowed to stand still for 15 minutes. In case of a tablet showing a "dissolution type disintegration pattern," the tablet melted from the surface portion and gradually disintegrated into fine powders and if the dish was slightly shaken, coarse blocky fragments were not formed.

(2) Swinging Method:
The disintegration test was carried out in a disintegration tester. In case of a tablet showing a "dissolution type disintegration pattern," the tablet dissolved from the surface and gradually thinned without block fragments being left during disintegration.

Dissolution Speed:
The dissolution speed was determined according to the rotary basket method disclosed in the specification of U.S. Pat. No. 3,622,677. A dissolution medium (0.1 N HCl) was maintained at 37°±1° C. and 2 ml of the sample liquid was collected at predetermined intervals through a membrane filter. The sample liquid was diluted so that the concentration was reduced to 1/50, and the absorbance at a wavelength of 245 nm was measured by using a UV meter and the dissolution quantity was determined according to the calibration curve method. The measurement of the dissolution speed was repeated 5 times on the same tables and the average value was calcultated.

TABLE 3

Results of Evaluation of Physical Properties of Tablets

| Sample | Compression Force (Kg/cm²) | Coefficient of Variance (CV Value, %) | Hardness (Kg) | Disintegration Time (minutes) | Disintegration Pattern |
|---|---|---|---|---|---|
| Examples of Present Invention | | | | | |
| A-1 | 500 | 2.2 | 5.3 | <1 | Dissolution |
| | 1000 | 2.3 | 8.1 | 2.1 | type |
| A-2 | 500 | <2 | 5.5 | <1 | Dissolution |
| | 1000 | | 8.2 | 1.8 | type |
| A-3 | 500 | <1 | 5.6 | <1 | Dissolution |
| | 1000 | | 8.5 | 2.0 | type |
| B-1 | 500 | <2 | 4.8 | 2.5 | Slightly |
| | 1000 | | 7.9 | 3.1 | coarse fragments |
| B-2 | 500 | <2 | 5.0 | 1.2 | Dissolution |
| | 1000 | | 7.9 | 2.1 | type |
| C | 500 | <2 | 4.9 | <1 | Dissolution |
| | 1000 | | 7.3 | 1.5 | type |
| E | 500 | 2.4 | 4.3 | 1.4 | Dissolution |
| | 1000 | 2.4 | 7.1 | 2.9 | type |
| Comparative Examples | | | | | |
| D | 500 | 3.3 | 3.2 | 3.5 | Coarse |
| | 1000 | 3.5 | 5.8 | >15.0 | fragments |
| F | 500 | <2 | 5.1 | 3.0 | Coarse |
| | 1000 | | 8.0 | 6.4 | fragments |
| G | 500 | <2 | 3.8 | 2.6 | Coarse |
| | 1000 | | 6.9 | 5.8 | fragments |
| H | 500 | <2 | 4.4 | 2.9 | Coarse |
| | 1000 | | 7.8 | >15.0 | fragments |
| CS | 500 | 3.1 | 4.0 | 2.3 | Coarse Fragments |
| | 1000 | — | Capping | — | — |

TABLE 4

Dissolution Speeds of Tablets

| Sample | After 10 minutes | After 30 minutes | After 60 minutes |
|---|---|---|---|
| A-1 | 41.5% | 67.7% | 81.4% |
| A-2 | 39.3% | 68.1% | 82.0% |
| A-3 | 38.1% | 69.3% | 81.9% |
| B-1 | 27.0% | 54.4% | 72.2% |
| B-2 | 36.5% | 60.4% | 80.7% |
| C | 43.3% | 71.2% | 85.8% |
| E | 26.0% | 52.9% | 72.4% |
| D (comparison) | 14.4% | 54.8% | 69.1% |
| F (comparison) | 10.8% | 21.9% | 49.6% |
| G (comparison) | 7.7% | 22.9% | 48.4% |
| H (comparison) | 6.1% | 18.4% | 49.5% |
| CS (comparsion) | 18.4% | 27.4% | 46.2% |

Note
Sample tested were those molded under 1000 Kg/cm² except sample CS.

The table to shown in Table 3 were subjected to the accelerated stability test at a temperature of 40° C. and a relative humidity of 75% for 2 weeks. In tablets of the samples F, H, H and CS, the hardness was reduced and the disintegration time was drastically prolonged. On the other hands, in tablets of Samples A, B, C and E, the hardness was not substantially changed, or if the hardness was changed, the change was very slight.

EXAMPLE 6

To a composition comprising 400 parts of pharmacopoeial phenacetin, 200 parts of pharmacopoeial microcrystalline cellulose, 320 parts of pharmacopoeial fine lactose and 20 parts of hydroxypropyl cellulose (SL type supplied by Nippon Soda K.K.) were added 50 parts of each of the powdery samples shown in Table 2, and water was added to the mixture and granulation was then carried out according to customary procedures. The granulation product was dried and the size was adjusted. Then, 10 parts of pharmacopoeial magnesium stearate was mixed with 990 parts of the so-obtained dry granules, and the mixture was compressed in the same manner as described in Example 5. The physical properties of the tablets were evaluated. The obtained results are shown in Table 5, below.

TABLE 5

Results of Evaluation of Physical Propeties of Tablets

| Sample | Compression Force (Kg/cm²) | CV Value (%) | Hardness (Kg) | Disintegration Time (minutes) | Disintegration Pattern |
|---|---|---|---|---|---|
| A-1 | 500 | <2 | 4.8 | 1.4 | Dissolution |
| | 1000 | | 6.9 | 3.8 | type |
| A-2 | 500 | <2 | 4.6 | 1.2 | Dissolution |
| | 1000 | | 6.7 | 2.9 | type |
| A-3 | 500 | <2 | 4.8 | 1.6 | Dissolution |
| | 1000 | | 7.1 | 3.5 | type |
| B-1 | 500 | <2 | 3.7 | 2.2 | Slightly |
| | 1000 | | 6.5 | 4.5 | coarse fragments |
| B-2 | 500 | <2 | 4.3 | 1.8 | Dissolution |
| | 1000 | | 6.6 | 4.0 | type |
| C | 500 | <2 | 4.3 | <1 | Dissolution |
| | 1000 | | 6.5 | 2.8 | type |
| E | 500 | <2 | 4.1 | 2.2 | Dissolution |
| | 1000 | | 5.9 | 5.6 | type |
| D | 500 | <2 | 2.8 | 15.7 | Coarse |
| | 1000 | | 5.8 | >30 | fragments |
| F | 500 | <2 | 4.3 | >20 | Coarse |
| | 1000 | | 6.5 | >40 | fragments |
| G | 500 | <2 | 2.7 | 13.1 | Coarse |
| | 1000 | | 5.3 | >30 | fragments |
| H | 500 | <2 | 5.0 | >30 | Coarse |
| | 1000 | | 7.3 | >60 | fragments |
| CS | 1000 | <2 | 2.6 | 28 | Coarse |
| | 1000 | | 5.0 | >20 | fragments |

EXAMPLE 7

To a composition comprising 200 parts of pharmacopoeial powdery acetaminophen, 445 to 495 parts of pharmacopoeial crystalline lactose, 300 parts of pharmacopoeial microcrystalline cellulose and 5 parts of pharmacopeial magnesium stearate were added 0, 10 or 80 parts of sample A-1, D, F or CS shown in Table 2 or pharmacopoeial calcium carboxymethyl cellulose, and they were mixed according to customary procedures and directly tableted according to the method described in Example 5. The physical properties of the obtained tablets were evaluated. The obtained results are shown in Table 6, below.

TABLE 6

Results of Evaluation of Physical Properties of Tablets
(Molding Pressure = 500 Kg/cm²)

| Sample | Amount Added (parts) | CV Value (%) | Hardness (Kg) | Disintegration time (minutes) | Disintegration Pattern |
|---|---|---|---|---|---|
| A-1 | 0** | | 5.9 | >15 | Coarse fragments |
| | 10 | <2 | 5.8 | 4.1 | Dissolution type |
| | 80 | | 5.5 | <1.0 | Dissolution type |
| D | 0** | <2 | 5.9 | >15 | Coarse fragments |
| | 10 | 2.2 | 5.7 | 14.1 | Coarse fragments |
| | 80 | 3.4 | 4.3 | 8.4 | Coarse fragments |
| F | 0** | | 5.9 | >15 | Coarse fragments |

TABLE 6-continued

Results of Evaluation of Physical Properties of Tablets
(Molding Pressure = 500 Kg/cm$^2$)

| Sample | Amount Added (parts) | CV Value (%) | Hardness (Kg) | Disintegration time (minutes) | Disintegration Pattern |
|---|---|---|---|---|---|
| | 10 | <2 | 5.9 | 13.9 | Coarse fragments |
| | 80 | | 4.4 | 6.2 | Coarse fragments |
| CS | 0** | <2 | 5.9 | >15 | Coarse fragments |
| | 10 | <2 | 5.9 | >15 | Coarse fragments |
| | 80 | 3.7 | 5.1 | 12.2 | Coarse fragments |
| CMC—Ca* | 0** | <2 | 5.9 | >15 | Coarse fragments |
| | 10 | <2 | 5.8 | 6.3 | Coarse fragments |
| | 80 | 3.4 | 5.2 | <1.0 | Slightly coarse fragments |

Note
*CMC—Ca represents calcium carboxymethyl cellulose.
**The same data were used for all the samples.

EXAMPLE 8

A composition comprising 480 parts of pharmacopoeial lactose, 100 parts of pharmacopoeial corn starch, 395 parts of pharmacopoeial microcrystalline cellulose, 5 parts of pharmacopoeial magnesium stearate and 20 parts of hydroxypropyl cellulose was sufficiently mixed, and water was added and granulation was carried out according to customary procedures. The granulation product was dried and passed through a 24-mesh sieve to remove coarse granules. Then, 60 parts of a disintegrant was added to 1000 parts of the so-obtained granules and the mixture was compressed according to the method described in Example 5. Samples A-2, F, G, H and CS shown in Table 2 were independently used as the disintegrant. The physical properties of the obtained placebo tablets were evaluated. The obtained results are shown in Table 7.

TABLE 7

Results of Evaluation of Physical Properties of Tablets

| Sample | Compression Force (Kg/cm$^2$) | CV Value (%) | Hardness (%) | Disintegration Time (minutes) | Disintegration Patter |
|---|---|---|---|---|---|
| A-2 | 750 | <2 | 6.4 | <1 | Dissolution type |
| | 1500 | | 11.3 | 3.2 | |
| F | 750 | <2 | 4.8 | 2.0 | Coarse fragments |
| | 1500 | | 5.2 | 5.7 | |
| G | 750 | <2 | 4.3 | 3.8 | Coarse fragments |
| | 1500 | | 5.9 | 7.0 | |
| H | 750 | <2 | 5.8 | 12.4 | Coarse fragments |
| | 1500 | | 6.2 | 15.8 | |
| CS | 750 | 2.2 | 4.2 | 1.9 | Coarse fragments |
| | 1500 | 2.4 | Capping | — | — |

Comparative Example 5

In 470 ml of water was dispersed 30 g of corn starch, and the temperature was elevated to 88° C. at a temperature-elevating rate of 1.5° C./min. When the temperature was elevated to 88° C., the dispersion was immediately placed in a refrigerator maintained at 5° C. and was allowed to stand still in this refrigerator for 20 hours to age the starch. The aged starch dispersion was dried by hot air maintained at 80° C. and the dried produce was pulverized to obtain processed corn starch.

The swelling volume of the obtained sample was large and about 9.2 ml/g, but when the sample was observed by a microscope, the shell film structure inherent in green starch granules was not found. When the sample was compressed by wet granulation according to the method described in Example 8, both the hardness and disintegration degree of the obtained tablets were outside the permissible ranges.

Comparative Example 6

Potato starch having a water content of 19% by weight was subjected to a wet heat treatment at 120° C. for 120 minutes in a closed system vessel. The vessel was opened and the obtained sample I was collected.

Since the sample I consisted substantially of coarse granules having a size larger than 60 mesh, the sample was pulverized and a fraction capable of passing through a 60-mesh sieve was collected. The physical properties of the so-called sample were evaluated. It was found that the sample was characterized by a bulk density of 0.49 g/cc, a cold water-soluble component content of 9.3% an expanded volume of 5.6 ml/g and a water retention of 2.8 and the sample contained about 30% of birefringent granules.

The sample was compressed by wet granulation according to the method described in Example 8. The obtained tablets had a hardness of about 4 to about 5 Kg and were satisfactory in the hardness, but the degree of integration was outside the permissible range.

EXAMPLE 9

Corn starch was dispersed at a concentration of 10% by weight in an aqueous medium containing 50, 65 or 80% by weight of ethanol and the respective dispersions were heated at 90°, 115° or 140° C. for about 20 minutes in an autoclave equipped with a stirrer.

The so-obtained three products were filtered and air-dried so that the liquid content was reduced below 4%, and the dried products were pulverized to obtain samples J, K and L. The physical properties of these samples are shown in Table 8. It was found that these samples had physical properties similar to those of the samples A-1, A-2, A-3, B-1, B-2, C and E obtained by performing heating in the presence of water alone.

TABLE 8

Results of Evaluation of Physical Properties of Various Samples

| Sample | Content (%) of Residue on 60-Mesh Sieve | Bulk Density (g/cc) | Cold Water-Soluble Component Content (%) | Swelling Volume (ml/g) | Birefringent Characteristics | Destruction of Granules | Water Retention |
|---|---|---|---|---|---|---|---|
| J | 1.3 | 0.45 | 3.4 | 11.3 | No substantial polarizing cross hairs | Violet color | 5.7 |

TABLE 8-continued

Results of Evaluation of Physical Properties of Various Samples

| Sample | Content (%) of Residue on 60-Mesh Sieve | Bulk Density (g/cc) | Cold Water-Soluble Component Content (%) | Swelling Volume (ml/g) | Birefringent Characteristics | Destruction of Granules | Water Retention |
|---|---|---|---|---|---|---|---|
| K | 0.4 | 0.48 | 2.9 | 10.9 | No substantial polarizing cross hairs | Violet color | 5.9 |
| L | 0.1 | 0.52 | 2.7 | 11.4 | No substantial polarizing cross hairs | Violet color | 5.9 |

Sample K was selected as a typical sample and was wet-tableted according to the method described in Example 8. The physical properties of the obtained tablets were evaluated. The obtained results are shown in Table 9, below.

It is seen that also in products obtained by performing the treatment of the present invention by using an alcohol/water mixed medium, the intended effects of the present invention can be attained.

TABLE 9

Results of Evaluation of Physical Properties of Tablets

| Sample | Compression Force (Kg/cm²) | CV Value (%) | Hardness (Kg) | Disintegration Time (minutes) | Disintegration Pattern |
|---|---|---|---|---|---|
| K | 750 | <2 | 6.5 | <1 | Dissolution type |
|   | 1500 |   | 8.2 | 2.9 |   |

EXAMPLE 10

Dyeing was conducted on samples A-1, B-2, F, G, H and CS listed in Table 2 by the following procedures, and color differences were measured.

A centrifugal sedimentation tube having a capacity of 50 ml was charged with 1 g of the starch sample and 6 ml of a 1% aqueous solution of Safranine O/ethanol (70/100) was added, and the mixture was sufficiently stirred by a glass rod and allowed to stand still for 15 minutes to effect dyeing.

Deionized water was added, and centrifugal separation and decantation were repeated 5 times to wash away the excessive dye.

Then, a 1% solution of Nippon Sky Blue was added to the charge of the tube until a homogeneous mixture was obtained, and the mixture was stirred and subjected to filtration washing under suction with pure water by using an ordinary qualitative test filter paper (No. 1 supplied by Toyo Roshi K.K., 6 microns). This washing was repeated until the filtrate became semitransparent. Then, the obtained wet filter cake was transferred to an appropriate holder and excessive water present on the surface was absorbed on a filter paper and thus removed. Then, color difference of the Lab system were measured according to the method of JIS Z-8730 by using a direct-reading color difference computer, Model CDE-S CH-GV4 (supplied by Suga Tester K.K.).

The measurement results are shown in Table 10, below.

TABLE 10

Results of Measurements of Color Differences

| Sample | L | a | b | ΔE(Lab) |
|---|---|---|---|---|
| A-1 | 25.9 | 12.2 | −14.5 | 70.2 |
| B-1 | 27.7 | 8.4 | −17.3 | 68.6 |
| F | 28.3 | 14.3 | −11.0 | 67.4 |
| CS | 36.2 | 24.1 | −4.2 | 62.1 |

Note
Reference Sample (white plate):
L = 92.3, a = 1.4, b = 3.7

In case of the samples G and H, the viscosity was increased presumably because the cold water-soluble components were gradually swollen and dissolved during the step of washing away the dye, and therefore, filtration was impossible and the color differences could not be measured. On the other hand, in case of the processed starch of the present invention, filtration could be performed very smoothly.

When the data shown in Table 10 are plotted on Lab chromaticity coordinates, it is apparent that the chromaticity characteristics of the sample F are closer to those of the sample CS, that is, the starting corn starch, than to those of the samples A-1 and B-1. Since damaged starch granules or cold water-soluble portions were washed away when excessive Safranine O was removed by decantation, the blue-dyed portion was decreased and the hue of the sample became close to the hue of the sample CS.

For the foregoing reasons, the color differences of the samples G and H could not be measured. However, water-containing viscous pastes of these samples showed a deep blue color.

Comparative Example 7

Potato starch was treated according to the procedures described in Example 3 to obtain a sample M. Incidentally, the heating temperature was charged to the predetermined temperature (i.e., 61.5° C.).

The sample M had a bulk density of 0.48 g/cc, a cold water-soluble component content of 13.4%, a swelling volume of about 16 ml/g and a water retention of about 5.2. No polarizing cross hairs were observed.

The sample M was tableted according to the method described in Example 5. The hardness was sufficient, but the disintegration time was long (more than 15 minutes in case of tablets molded under a molding pressure of 1000 Kg/cm²) and the disintegration pattern was not good. Moreover, the dissolution speed of the active ingredient from the tablets was very low, that is, 9.1% after 10 minutes, 19.9% after 30 minutes and 56.2% after 60 minutes.

EXAMPLE 11

The disintegration time and dissolution rate of the granules obtained in Example 6 were determined. The obtained results are shown in Table 11, below.

TABLE 11

Results of Evaluation of Physical Properties of Granules

| Sample | Disintegration Time (minutes) | Dissolution Rate (%) After 10 minutes | After 30 minutes | After 60 minutes |
|---|---|---|---|---|
| A-1 | <3 | 48.3 | 74.5 | 83.3 |
| A-2 | <3 | 42.1 | 70.4 | 83.9 |
| A-3 | <3 | 43.6 | 74.2 | 83.8 |
| B-1 | 3.5 | 29.9 | 56.5 | 75.4 |
| B-2 | 3.7 | 39.7 | 65.2 | 81.1 |
| C | <3 | 47.4 | 72.1 | 88.0 |
| E | 3.8 | 30.0 | 56.1 | 75.4 |
| D | >10 | 19.9 | 50.3 | 72.4 |
| F | >10 | 13.2 | 29.9 | 56.1 |
| G | 10 | 8.1 | 27.4 | 52.8 |
| H | 20 | 9.9 | 22.2 | 50.6 |
| CS | 20 | 17.2 | 29.7 | 50.5 |

We claim:

1. A processed starch derived from a terrestrial starch and consisting essentially of substantially non-birefringent starch powder which substantially retains a shell film structure of green starch granule, said starch powder having a particle size distribution substantially free of a fraction having a size of 48 Tyler standard sieve mesh or having a larger size and said starch powder having a bulk density of at least 0.25 g/cc, a cold water-soluble component content of less than 5% by weight, a swelling volume of about 3 to about 15 ml/g and a water retention of at least about 2.

2. A processed starch as set forth in claim 1, wherein the swelling volume is about 7 to about 15 ml/g and the water retention is at least about 3.

3. A processed starch as set forth in claim 1, wherein the starch is corn starch.

4. A processed starch as set forth in claim 1, wherein at least 95% by weight of the starch powder passes a 60-mesh sieve.

5. A processed starch derived from a terrestrial starch and consisting essentially of substantially non-birefringent starch powder which substantially retains a shell film structure of green starch granule, said starch powder having a particle size distribution substantially free of a fraction having a size of 48 Tyler standard sieve mesh or having a larger size and said starch powder having a bulk density of at least 0.25 g/cc, a cold water-soluble component content of less than 5% by weight, a swelling volume of about 3 to about 15 ml/g and a water retention of at least about 2, said starch being prepared by the steps comprising:

adding water and an optional organic solvent to green terrestrial starch to form a dispersion having a solid component concentration of not more than 30% by weight;

heating the dispersion at a temperature higher than 50° C. but not exceeding the temperature of 10° C. higher than the gelatinization-starting temperature of the starch particles in the dispersion, whereby the green terrestrial starch granule is swollen without destruction of the shell film structure thereof and rendered non-birefringent, and then drying the dispersion without destruction of said shell film structure.

6. A method for imparting a disintegrating property to a medicine, which comprises adding a processed starch singly or together with other pharmaceutical additives to the medicine, said processed starch being derived from a terrestrial starch and consisting essentially of substantially non-birefringent starch powder which substantially retains a shell film structure of green starch granule, said starch powder having a particle size distribution substantially free of a fraction having a size of 48 Tyler standard sieves mesh or having a large size and said starch powder having a bulk density of at least 0.25 g/cc, a cold water-soluble content of less than 5% by weight, a swelling volume of about 3 to about 15 ml/g and a water retention property of at least about 2.

7. A method for imparting a disintegrating property to a medicine according to claim 6, wherein the processed starch has a swelling volume of about 7 to about 15 ml/g and a water retention of at least about 3.

8. A method for imparting a disintegrating property to a medicine according to claim 6, wherein the starch is corn starch.

9. A method for imparting a disintegrating property to a medicine according to claim 6, wherein the processed starch is added in an amount of at least 1% by weight based on the medicine.

10. A method for imparting a disintegrating property to a medicine according to claim 6, wherein the processed starch is added to the medicine together with microcrystalline cellulose.

* * * * *